United States Patent

Baruch et al.

Patent Number: 5,209,719
Date of Patent: May 11, 1993

[54] ULTRASONIC RECANALIZATION SYSTEM

[75] Inventors: David Baruch, Tel Aviv; Shmuel Einav, Hertzlia, both of Israel

[73] Assignee: Urcan Medical Ltd., Tel-Aviv, Israel

[21] Appl. No.: 643,427

[22] Filed: Jan. 22, 1991

[30] Foreign Application Priority Data

Jan. 23, 1990 [IL] Israel .................................... 093141

[51] Int. Cl.$^5$ .............................................. A61B 17/20
[52] U.S. Cl. .................................. 604/22; 128/24 AA
[58] Field of Search ............ 128/24 AA, 657; 604/22; 606/169–171

[56] References Cited

U.S. PATENT DOCUMENTS

| | | | |
|---|---|---|---|
| 3,526,219 | 9/1970 | Balamuth | 604/22 |
| 4,030,503 | 6/1977 | Clark, III | 604/22 |
| 4,063,557 | 12/1977 | Wuchinich et al. | 604/22 |
| 4,526,571 | 7/1985 | Wuchinich | 604/22 |
| 4,616,653 | 10/1986 | Samson et al. | 128/657 |
| 4,631,052 | 12/1986 | Kensey | 604/22 |
| 4,634,419 | 1/1987 | Kreizman et al. | 604/22 |
| 4,768,496 | 9/1988 | Kreizman et al. | 604/22 |
| 4,832,047 | 5/1989 | Sepetka et al. | 128/657 |
| 4,846,186 | 7/1989 | Box et al. | 128/657 |
| 4,867,141 | 9/1989 | Wakada et al. | 604/22 |
| 4,870,953 | 10/1989 | Don Michael et al. | 604/22 |
| 4,974,581 | 12/1990 | Wiksell | 604/22 |
| 4,998,527 | 3/1991 | Meyer | 604/22 |
| 5,025,799 | 6/1991 | Wilson | 128/657 |
| 5,058,570 | 10/1991 | Idemoto et al. | 604/22 |

FOREIGN PATENT DOCUMENTS

| | | | |
|---|---|---|---|
| 0316796 | 5/1989 | European Pat. Off. | 604/22 |
| 0443256 | 8/1991 | European Pat. Off. | |
| 3705339 | 9/1988 | Fed. Rep. of Germany | 604/22 |
| 8816114 | 9/1989 | Fed. Rep. of Germany | |
| 2302713 | 3/1976 | France | 604/22 |
| 87/05793 | 10/1987 | World Int. Prop. O. | |

Primary Examiner—Stephen C. Pellegrino
Assistant Examiner—Michael Rafa
Attorney, Agent, or Firm—Charles E. Baxley

[57] ABSTRACT

An ultrasonic recanalization system includes an ultrasonic transducer member energized by a switch and connected to a console containing control elements. The transducer transfers ultrasonic energy through a tube into a patient's artery through a triple lumen catheter. The tube has at its end a bent portion with a flexible tip and the catheter has a flow blocking device which is inflatable to secure the position of the tip of the hollowed tube in the artery and to obstruct the flow of blood near a stenosis site in the artery. A liquid solution can be pumped into a concentric canal passage around the hollowed tube and the solution can then flow out through the hollowed tube after washing off the stenosis splinters.

15 Claims, 3 Drawing Sheets

ULTRASONIC RECANALIZATION SYSTEM

BACKGROUND OF THE INVENTION

This invention relates to an ultrasonic recanalization system for ablation of atherosclerotic stenosis and plaques in human or animal atherosclerotic arteries, to be used in human or animal percutaneous and transcutaneous recanalization (angioplasty).

Several angioplasty techniques are known in the prior art. The most advanced techniques to date are those using balloon catheters, or those using laser angioplasty with specific laser systems, and those using a high speed rotary cutting blade technique.

The most advanced technologies in this art are described in the following documents:

EP 268,068 filed on 23 October 1986 describes an angioplasty balloon catheter.

Edwards Lis Division of Baxter has a commercial balloon catheter marketed as Hydracross ®.

Trimedyne Inc. has a laser angioplasty product marketed as Laserprobe ®.

U.S. Pat. No. 4,819,634 describes the use of the rotary blade catheter technique for atherectomy.

Lately scientists decided to apply ultrasonic techniques to recanalization (angioplasty).

Ultrasonic technology has been used widely in dentistry and there are many sophisticated techniques for applying ultrasonic transducers to different probes having to penetrate tissues inbetween teeth or gums. The modern equipment is supplied with efficient cooling systems and controls for both temperature frequency and amplitude of the ultrasonic energy emitted at the probe tips.

In surgery, ultrasonic technology has been used for many years; equipment such as Storz ultrasonic nephroscopic sheath (produced by Storz Endoscopy-America Inc.) has been used for a long while in urology for percutaneous nephrolithotomy to disintegrate calcium blocks. Saline at 4° C. is used for cooling the overheated probe.

The complete procedure is discussed in an article published by M. G. Eugaras et al. in "The Journal of Thoracic and Cardiovascular Surgery 1988" 95:1038–40 demonstrating the advantage of the ultrasonic system.

Using double or triple lumen catheters to enter arteries and perform recanalization procedures by either of the known arts (balloon or laser) or by rotational thrombectomy, using a high speed rotary cutting blade inserted through a catheter into the artery, the blade minces the stenosis obstruction and, consequently enlarges the artery lumen. At this point, the technique of using the balloon can be applied. It was therefore an obvious development in the art to try to apply the sophisticated ultrasonic technology, using a double or triple lumen catheter with the modified ultrasonic probes to perform recanalization in arteries The use of an ultrasonic angioplasty system is described in detail by R. Seigal et al., who published a detailed report "Ultrasonic Plaque Ablation for Recanalization or Occluded Arteries." The report was published in "Circulation," p. 1443, in December 1988.

C. Dobrinski et al. published their work on "Ultrasonic Angioplasty" in the journal "Archive des Maladies du Coeur," 1989; 82;377–80.

EP 316,796 published 24 May 1989 describes an ultrasonic device having an ultrasonic generator connected to a probe extending from the end of a catheter. The bulbous tip of the probe is placed against the blockage. A radiographic contrast fluid can be introduced into the catheter to make the blood vessel clearly visible on an X-ray monitor.

U.S. Pat. No. 4,808,153 published 28 February 1989 describes a device for removing plaque from arteries. The vibrations are transferred through a hollow member of an inert rigid material such as titanium. Several vibrating members are disposed around the hollow member, all activated by the ultrasonic frequency. A flexible catheter is disposed on the hollowed member, having a forward end covering the hollow member ending and having a blunt disposition.

WO 8,906,515 published 27 July 1989 describes an ultrasonic angioplasty device that employs a frequency generator, a piezoelectric transducer, and a horn. An ultrasonic transmission member is used to introduce the device into the patient's circulatory system. The ultrasonic transmission member is formed as a wire of aluminum or similar alloy in an annealed state.

In all these prior art works, it was clearly demonstrated that the ultrasonic technique for angioplasty is viable if carried out carefully without risking any damage to the inner surface of the arteries during the application and specifically when approaching the stenosis blocked sites, and, if appropriate, cooling is provided.

It is therefore the purpose of this invention to provide an ultrasonic recanalization system having sufficient controls and specific applicators which will minimize the risk of damage to the arteries before, during and after the ultrasonic ablation of the atherosclerotic plaques, as well as to assure that the stenosis splinters released during the application will not block the ultrasonic hollowed tip. The ultrasonic tip has appropriate cooling means on the inner and outer lumen.

The ultrasonic recanalization technique provided will enable ablation of peripheral and coronary atherosclerotic arteries in humans and animals. It may also be used in urology service for percutaneous nephrolithomy decalcification, as well as decalcification of blockages in the pancreas, etc.

SUMMARY OF THE INTENTION

The inventive ultrasonic recanalization system comprises an ultrasonic transducer in a handle and energized by a switch. The transducer member connected to an ultrasonic console containing control means of the ultrasonic energy level applied, determined by a measuring device of the frequency and amplitude provided at tip ending of the transducer. The ultrasonic transducer transfers the ultrasonic energy through a hollowed tube entered into the patient's arteries through a triple lumen catheter, and the ultrasonic tube has at its ending a bent portion with a flexible tip. The triple lumen catheter has a flow blocking device such as a balloon on the outer circumference of its tip which can be inflated when required to secure the catheter in position and block the flow of blood near the stenosis blockage site in the artery and having a concentric canal passage around the ultrasonic hollowed tube through which a liquid solution can be pumped in from a reservoir by a pump in the ultrasonic console. The solution can then flow out after washing off the stenosis splinters and blood into a second reservoir provided in the console, though the hollowed tube.

In the preferred embodiment, the ultrasonic hollowed tip ending is provided with a spring having high flexibility to enable the user to have maximal adaptation to variations of movement of the ultrasonic tube inside the arteries, specifically when reaching contact with rigid stenosis or plaque blockages, or when reaching contact with a soft flexible artery inner surface. The tip ending prevents perforation of the artery.

In the preferred embodiment, the hollowed tube is provided with an ending in form of a three-cheek rotor preventing blockage of the hollowed tube by stenosis being sucked out therethrough.

In the preferred embodiment the ultrasonic hollowed tube and tip are made of a rigid material longitudinally, and flexible in all other directions with an inner and outer special protection coating such as Teflon ® or a similar inert, tough, and smooth material.

In the preferred embodiment the ultrasonic console comprises frequency, gain and flow control knobs to be set manually by the user at the required levels.

In the preferred embodiment the ultrasonic console contains a computerized automatic control system set by a computer program that controls the ultrasonic energy level transmitted by the ultrasonic transducer and the flow rate of the solution pumped into the arteries by said positive displacement pump through the triple lumen catheter.

In the preferred embodiment, the reservoir containing the solution is part of the console, having also a temperature control assuring the appropriate required temperature of the solution, such temperature to be preferably 37° C.

In the preferred embodiment, the solution is a saline with a specific appropriate cleaning chemical and an agent avoiding excess oxygen buildup. The solution could also contain strained blood suitable to be pumped into the artery to wash out the stenosis splinters after ultrasonic energy is applied. In the preferred embodiment the inward flow of the solution through the outer lumen of the triple lumen catheter, and the outward flow of the washout splinters of the stenosis with the blood and solution is through the inner lumen of the hollowed tube. Thus, the counterflow system acts as a cooling medium to the ultrasonic system.

In the preferred embodiment a second thermocouple is provided at the distal end of the ultrasonic hollowed tip, which will alert the system in case of excess temperature buildup in the proximal tip end endangering the artery tissue.

In the preferred embodiment, the ultrasonic handle includes the ultrasonic transducer which is energized by a switch mounted on the handle, and the strain gauge measuring the frequency and amplitude of the ultrasonic tip is mounted on the exit of the tip from the handle.

In the preferred embodiment, the balloon at the tip ending of the triple lumen catheter is inflated by a syringe connected by an air connecting tube to an entry adaptor of the triple lumen catheter.

In the preferred embodiment, the syringe is connected to the air tube through a control valve.

DESCRIPTION OF THE DRAWING

The invention can be best understood in reference to the attached drawings; in which.

DESCRIPTION OF THE INVENTION

Figure 1:
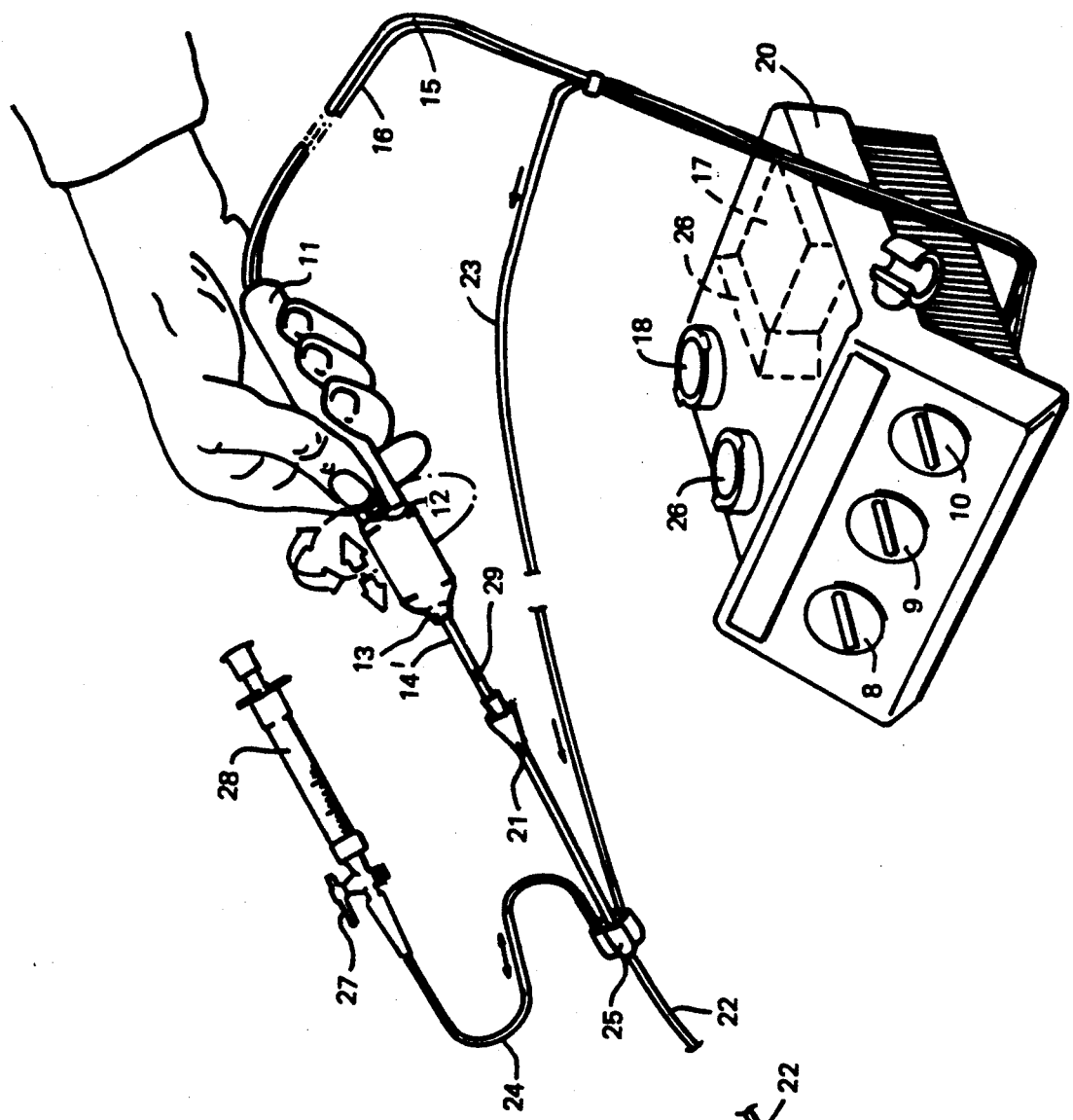
FIG. 1 is a three dimensional view of the complete system.
Figure 1A:
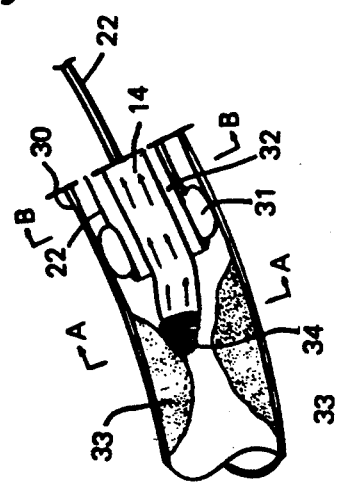
Figure 5:
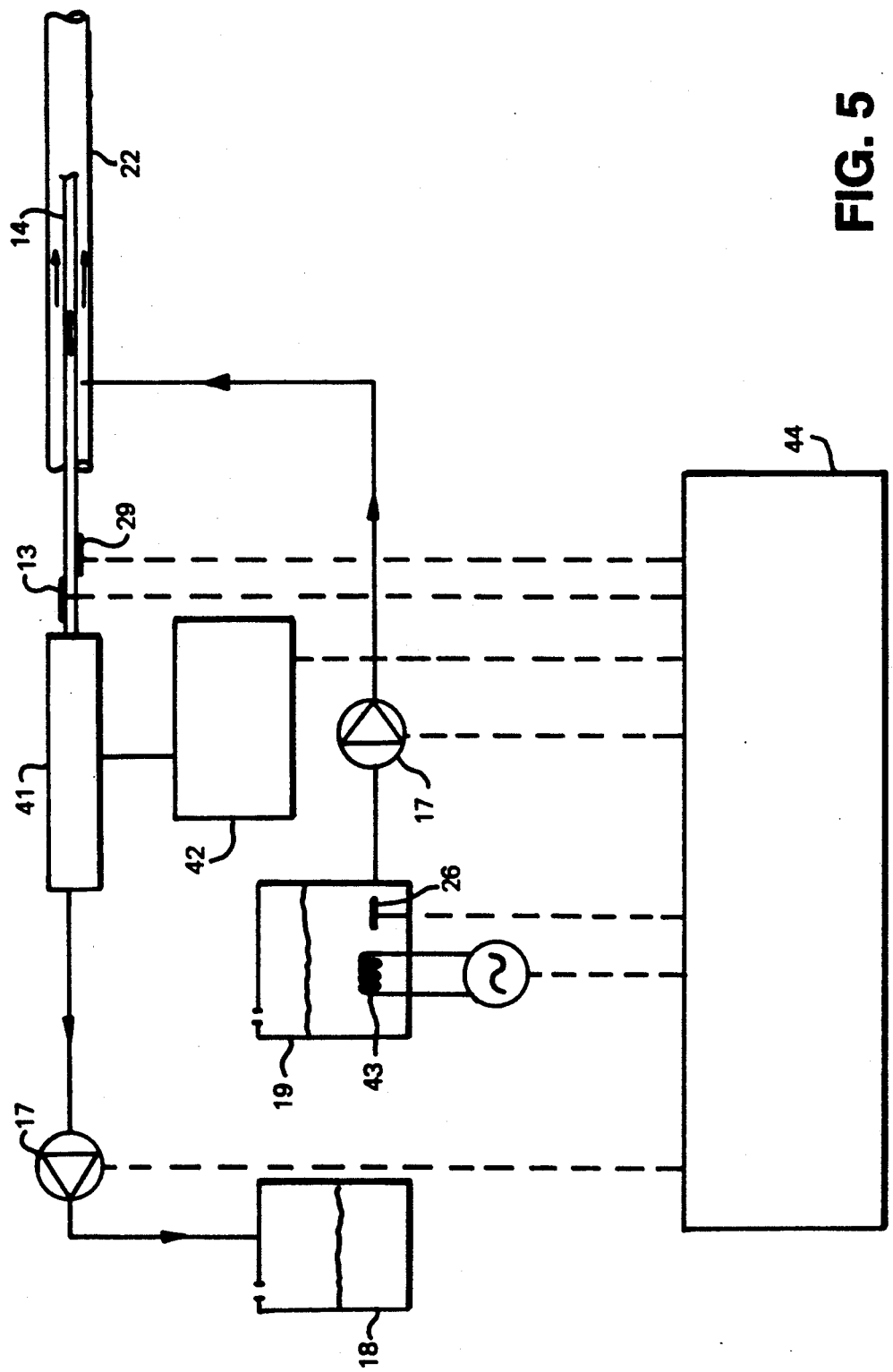
FIG. 5 is a control flow chart of the system.

FIG. 1 illustrates an ultrasonic transducer handle 11 comprising an ultrasonic transducer 41 seen schematically in FIG. 5) energized by a switch 12 mounted on the handle 11, which has at its tip a strain gauge 13 to measure the frequency and amplitude of the ultrasonic energy emitted through a hollowed tube 14 at the proximal tip ending in the artery. The gauge 13 transmits data to the ultrasonic control circuit 26 included in the console 20. The ultrasonic transducer 41 receives its power from an ultrasonic generator 42 placed in the console 20 through the cable 15. Three control knobs 8, 9, 10 are provided for manual control of frequency, power and liquid flow rate. Suction is applied through the hollowed tube 14 by a positive displacement pump 17 through a suction pipe 16 connecting the hollowed tube 14 to the console 20 to the wash-out liquid reservoir 18.

The hollowed tube 14 is placed into a guiding tube 21 leading the hollowed tube 14 into a triple lumen catheter 22 through the adapter 25. The adapter 25 is also connected to the air connecting pipe 24, and to the solution supply tube 23 which connects to the solution reservoir 19 in the console 20. The solution is pumped into the catheter 24 by the pump 17. The solution temperature is controlled by a temperature controller 26 assuring a required temperature (usually about 37° C.).

The air is forced into the triple lumen catheter 22 by a syringe 28 through an air control valve 27. A temperature controller 29 is provided at the distal end of the hollowed tube 14 that controls the temperature buildup near the artery of the hollowed tube ending 34, seen in the lower lefthand corner of FIG. 1, where there is illustrated an enlarged section of the artery 30 showing the ending of the triple lumen catheter 22, having a balloon 31 on its outer circumference inflated by the syringe 28 as explained above. The ultrasonic hollowed tube 14 goes through the catheter 22 and has a circumferential canal 32 through which the solution is pumped in from the solution reservoir 19. The stenosis-plaque blocking the artery 30 is shown by 33. The hollowed tube ending is shown by 34.

Figure 2:
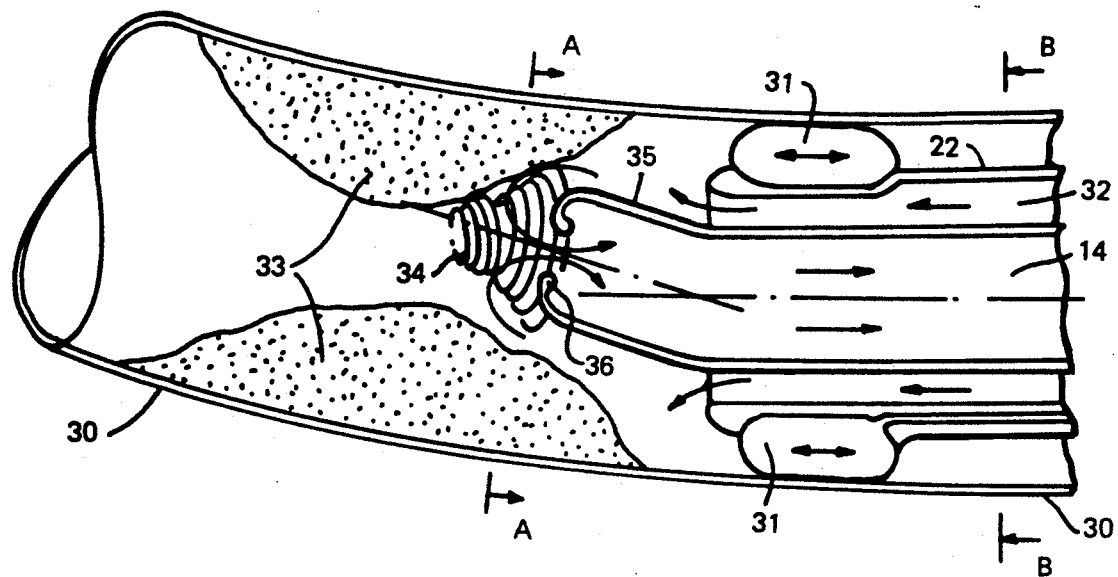
FIG. 2 is a longitudinal cross-section of the artery at the stenosis site, showing the ultrasonic hollowed tip.

FIG. 2 illustrates a more explicit cross-section of the artery 30 at the stenosis cleaning site.

The stenosis 33 blocks the artery 30. The catheter 22 has an outer balloon ring 31 securing its position and blocking the blood flow when the balloon 31 is inflated. The circumferential canal 32 allows inflow of the solution pumped in. The hollowed tube 14 passes through the central passage of the catheter 22. The hollowed tube 14 has an ending 34 in the form of a flexible spring, and the tube ending has a bent portion 35 with an ending 36 specifically designed to prevent flow blockage. Suction is applied through the hollowed tube 14 to suck out the blood solution and stenosis fragments after applying ultrasonic energy to tube 14.

Figure 3:
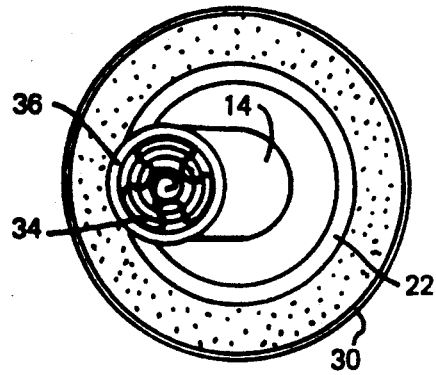
FIGS. 3 and 4 are two cross-sections of the artery and triple lumen catheter at different positions.

FIG. 3 illustrates the three-cheek rotor ending 36 of the hollowed tube 14, and the spring attachment 34.

Figure 4:
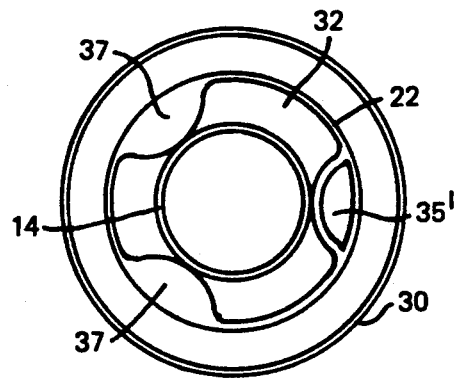

FIG. 4 illustrates the cross-section of the artery 30 showing the catheter 22 having a circumferential passage canal 32, and the air channel 35 for inflation and deflation of the balloon 31, and the hollowed tube 14 passing concentrically, guiding ribs 37 of catheter secure the concentric position of the hollowed tube 14.

FIG. 5 is a control flow chart of the system. The pump 17 has two heads. The first head pumps in solution from reservoir 19 through the outer lumen canal of the catheter 22, and the second head pumps out the washout liquids by suction containing the stenosis splinters, through the hollowed tube 14, into the reservoir 18.

The temperature of the solution in reservoir 19 is controlled by a thermocouple 26 which activates the heating element 43. A constant temperature of 37° C. is kept under regular conditions.

The ultrasonic transducer 41, placed inside the handle 11 (not seen in FIG. 5), receives its power from an ultrasonic generator 42 placed inside the console 20 (not seen in FIG. 5 but seen in FIG. 1), through the cable 15 (not seen in FIG. 5 but seen in FIG. 1). The strain gauge 13 controls the frequency and amplitude of the ultrasonic energy at the tip of the hollowed tube 14, and the thermocouple 29 controls the temperature of the outflowing wash liquid at the exit of the hollowed tube 14. When the temperature exceeds a set level, an alert is triggered. The control circuit 44, situated inside the console 20, is connected with the pump 17, the heating element 43 and thermocouples 26 and 29, and with the ultrasonic generator 42 and the strain gauge 13.

While the invention has been described in reference to the attached drawings, it should be appreciated that other ultrasonic recanalization systems can be built using the key features of this invention. They should all be regarded as being part of the invention.

What is claimed is:

1. An ultrasonic recanalization system comprising an ultrasonic transducer in a handle and energized by a switch, said transducer connected at its proximal end to a console containing control means of the ultrasonic energy level applied, determined by a measuring device of the frequency and amplitude provided at the distal end of the transducer, a triple lumen catheter that can be entered into a patient, and a hollowed tube which can be entered into the patient's artery through said catheter, said hollowed tube operatively connected to said transducer for receiving ultrasonic energy and transferring such energy into the patient's artery, said tube having an ending with a bent portion having a flexible tip, and said catheter having a flow blocking device on its outer circumference which includes means for inflating when required to secure said tip in position and obstruct the flow of blood near a stenosis blockage site in the artery, and said catheter having a concentric canal passage for surrounding said hollowed tube through which a liquid solution can be pumped in from a reservoir by a pump provided in said console, said hollowed tube including aspiration means whereby said solution can then flow out after washing off the stenosis splinters and blood into a second reservoir provided in said console, through said hollowed tube.

2. An ultrasonic recanalization system as in claim 1 wherein said ending of said hollowed tube is provided with a spring having high flexibility to enable maximal adaptability to movement variation of said tube in the arteries, giving different reactions when in contact with rigid stenosis or plaque blockage, or with soft artery tissue.

3. An ultrasonic recanalization system as in claim 1 wherein said hollowed tube ending is provided with a three-cheek rotor, preventing blockage of said hollowed tube ending by stenosis fragments.

4. An ultrasonic recanalization system as in claim 1 wherein said flow blocking device on said triple lumen catheter is a balloon.

5. An ultrasonic recanalization system as in claim 1 wherein said console comprises three knob controls to control manually the frequency, gain and flow levels of the ultrasonic transducer, and the solution liquid supply.

6. An ultrasonic recanalization system as in claim 1 wherein a computerized control circuit is provided in said console, having a computer programme for controlling the ultrasonic energy level transmitted by said ultrasonic transducer, and the flow rate of said solution pumped in through said triple lumen catheter in reference to the temperature of the washout liquid sucked out through said hollowed tube.

7. An ultrasonic recanalization system as in claim 1 wherein said reservoir containing said solution is included in the console and the hollow tube is provided with a temperature controller to secure the desired solution temperature.

8. An ultrasonic recanalization system as in claim 1 wherein said solution is saline containing appropriate chemicals for cleaning the artery treated by the ultrasonic tube, as well as applying an agent to avoid overreaction to sudden increase in oxygen content 9. An ultrasonic recanalization system as in claim 7 wherein said solution also contains strained blood 10. An ultrasonic recanalization system comprising an ultrasonic transducer in a handle and energized by a switch, said transducer connected at its proximal end to a console containing control means of the ultrasonic energy level applied, determined by a measuring device of the frequency and amplitude provided at the distal end of the transducer, a triple lumen catheter that can be entered into a patient, and a hollowed tube which can be entered into the patient's artery through said catheter, said hollowed tube operatively connected to said transducer for receiving ultrasonic energy and transferring such energy into the patient's artery, said tube having an ending with a bent portion having a flexible tip, and said catheter having a flow blocking device on its outer circumference which includes means for inflating when required to secure said tip in position and obstruct the flow of blood near a stenosis blockage site in the artery, and said catheter having a concentric canal passage for surrounding said hollowed tube through which a liquid solution can be pumped in from a reservoir by a pump provided in said console, said hollowed tube including aspiration means whereby said solution can then flow out after washing off the stenosis splinters and blood into a second reservoir provided in said console, through said hollowed tube, wherein the inward flow of said solution is through the outer lumen of said triple lumen catheter, and the outward flow of said wash-out liquid containing the stenosis splinters with blood is through the inner lumen of said hollowed tube, thus providing a cooling system to the tip of said hollowed tube, emitting ultrasonic energy in the artery.

11. An ultrasonic recanalization system as in claim 1 wherein said ultrasonic transducer is in a handle and energized by a switch mounted on said handle, or on a pedal.

12. An ultrasonic recanalization system as in claim 1 wherein a strain gauge measuring the frequency and amplitude at said hollowed tube tip is mounted at the proximal end of said hollowed tube.

13. An ultrasonic recanalization system as in claim 1 wherein said catheter has an adaptor and said balloon at the proximal ending of said catheter is inflated by a syringe connected through an air connecting tube to said adaptor of said triple triple catheter.

14. An ultrasonic recanalization system as in claim 1 wherein said hollowed tube and its tip are made, of a material that is longitudinally rigid but flexible in all other directions.

15. An ultrasonic recanalization system as in claim 1 wherein a thermocouple is provided at the distal ending of said hollowed tube, which causes an alert when an excess temperature is recorded, indicating potential danger at the ultrasonic tip in the proximal position near the artery.

* * * * *